United States Patent
Burkett

(10) Patent No.: US 9,924,903 B2
(45) Date of Patent: Mar. 27, 2018

(54) PRESSURE-SENSING GUIDE WIRE WITH SLIDING PRESSURE SENSOR

(71) Applicant: Volcano Corporation, San Diego, CA (US)

(72) Inventor: David H. Burkett, Temecula, CA (US)

(73) Assignee: VOLCANO CORPORATION, San Diego, CA (US)

(*) Notice: Subject to any disclaimer, the term of this patent is extended or adjusted under 35 U.S.C. 154(b) by 998 days.

(21) Appl. No.: 14/135,326

(22) Filed: Dec. 19, 2013

(65) Prior Publication Data
US 2014/0187979 A1    Jul. 3, 2014

Related U.S. Application Data

(60) Provisional application No. 61/746,537, filed on Dec. 27, 2012.

(51) Int. Cl.
*A61B 5/02* (2006.01)
*A61B 5/00* (2006.01)
*A61B 5/0215* (2006.01)
*A61B 8/12* (2006.01)

(52) U.S. Cl.
CPC .............. *A61B 5/6847* (2013.01); *A61B 5/02* (2013.01); *A61B 5/0215* (2013.01); *A61B 8/12* (2013.01)

(58) Field of Classification Search
CPC ....... A61B 5/02; A61B 5/0215; A61B 5/6847; A61M 2005/3201; A61M 2005/3243; A61M 2005/3295; A61M 2005/3297; A61M 2005/0175
See application file for complete search history.

(56) References Cited

U.S. PATENT DOCUMENTS

2002/0115982 A1* 8/2002 Barbut ................. A61B 5/0215 604/509
2006/0058653 A1* 3/2006 Sathyanarayana ... A61B 5/0215 600/437

\* cited by examiner

*Primary Examiner* — Puya Agahi

(57) ABSTRACT

An intravascular sensor assembly including a flexible elongate member having a longitudinal axis (LA) is provided. The sensor assembly includes a first engagement feature proximal to a distal end of the flexible elongate member; a core member disposed inside a lumen of the flexible elongate member, the core member configured to translate within the flexible elongate member along the LA proximal to the first engagement feature; and a component holding a sensor circuit, the component fixedly secured to a distal end of the core member such that the mounting structure translates along the LA of the flexible elongate member with the core member. A system and a method for performing measurements using a sensor as above are also provided.

7 Claims, 9 Drawing Sheets

PRESSURE-SENSING GUIDE WIRE WITH SLIDING PRESSURE SENSOR

CROSS-REFERENCE TO RELATED APPLICATIONS

The present application claims priority to and the benefit of U.S. Provisional Patent Application No. 61/746,537, filed Dec. 27, 2012, which is hereby incorporated by reference in its entirety.

TECHNICAL FIELD

The present disclosure relates generally to intravascular devices, systems, and methods. In some embodiments, the intravascular devices are guide wires that include one or more electronic, optical, or electro-optical components that slide along the vessel.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Often intravascular catheters and guide wires are utilized to measure the pressure within the blood vessel, visualize the inner lumen of the blood vessel, and/or otherwise obtain data related to the blood vessel. To date, guide wires containing pressure sensors, imaging elements, and/or other electronic, optical, or electro-optical components have suffered from reduced performance characteristics compared to standard guide wires that do not contain such components. Existing pressure guide wires typically have a single pressure sensor located approximately 3 cm from the distal tip of the guide wire. The sensors are fixed in position, thus only able to sense pressure at different locations by moving the entire catheter such that the sensor is located in the desired positions. Thus, in existing pressure guide wires the catheter position is lost during pullback, requiring the physician to re-cross a distal lesion. Thus, it is desirable to pullback the sensor to provide pressure values along a vessel path, such as in vessels with multiple lesions or vessels with long, diffuse lesions.

Accordingly, there remains a need for improved intravascular devices, systems, and methods that include one or more electronic, optical, or electro-optical components.

SUMMARY

According to embodiments disclosed herein an intravascular sensor assembly may include a flexible elongate member having a longitudinal axis (LA); a first engagement feature proximal to a distal end of the flexible elongate member; a core member disposed inside a lumen of the flexible elongate member, the core member configured to translate within the flexible elongate member along the LA proximal to the first engagement feature; and a component holding a sensor circuit, the component fixedly secured to a distal end of the core member such that the mounting structure translates along the LA of the flexible elongate member with the core member.

According to some embodiments, a system for performing measurements using a sensor exposed to an intravascular environment may include an intravascular device having a guide wire, the guide wire including a flexible elongate member having a longitudinal axis (LA); a first engagement feature proximal to a distal end of the flexible elongate member; a core member disposed inside a lumen of the flexible elongate member, the core member configured to translate within the flexible elongate member along the LA proximal to the first engagement feature; and a component holding a sensor circuit, the component fixedly secured to a distal end of the core member such that the mounting structure translates along the LA of the flexible elongate member with the core member; an interface device coupled to the intravascular device; a control console including a processor circuit and a memory circuit; and a display unit.

According to some embodiments a method for obtaining a measurement of an intravascular environment may include disposing an intravascular device inside a blood vessel such that a distal end of the intravascular device is positioned adjacent to a region of interest; displacing a core member within a flexible elongate member along a longitudinal axis (LA) of the intravascular device to a different position while maintaining the flexible elongate member fixed relative to the blood vessel; and receiving a signal from a sensor circuit mounted on a distal end of the core member.

These and other embodiments of the present invention will be described in further detail below with reference to the following drawings.

BRIEF DESCRIPTION OF THE DRAWINGS

In the figures, elements having the same reference number have the same or similar functions.

DETAILED DESCRIPTION

Figure 1:
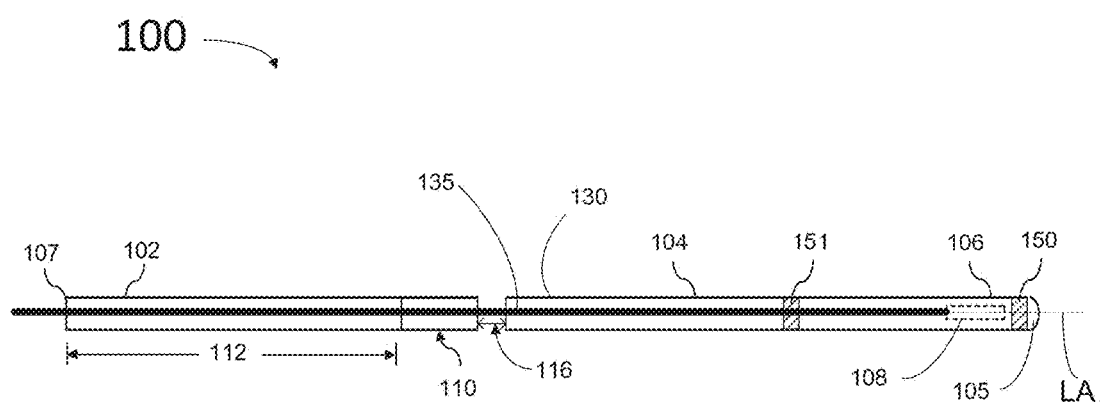
FIG. 1 is a diagrammatic, schematic side view of an intravascular device according to some embodiments.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, guide wires and catheters. In that regard, catheters may or may not include a lumen extending along its length for receiving and/or guiding other instruments. If the catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a temperature sensor, an imaging element, an optical fiber, an ultrasound transducer, a reflector, a mirror, a prism, an ablation element, an RF electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized.

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member, such as a guide wire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm) and approximately 0.018" (0.4572 mm)). In some embodiments, wires having 0.035" (0.889 mm) may be used. As such, the flexible elongate members incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an member is directly secured to another element, such as being glued or otherwise fastened directly to, on, within, etc. another element, as well as indirect techniques of securing two elements together where one or more elements are disposed between the secured elements.

FIG. 1 is a diagrammatic, schematic side view of an intravascular device 100 according to some embodiments. Intravascular device 100 includes a flexible elongate member 130 having a distal portion 106 adjacent a distal end 105 and a proximal portion 102 adjacent a proximal end 107. Inside flexible elongate member 130, a core member 135 may slide relative to flexible member 130 along a longitudinal axis (LA) of intravascular device 100. A component 108 is positioned within the distal portion 106 of the flexible elongate member 130 proximal of the distal tip 105. Generally, component 108 is representative of one or more electronic, optical, or electro-optical components. In that regard, component 108 may include a pressure sensor, a temperature sensor, an imaging element, an optical fiber, an ultrasound transducer, a reflector, a minor, a prism, an ablation element, an RF electrode, a conductor, and/or combinations thereof. The specific type of component or combination of components can be selected based on an intended use of the intravascular device. In some instances, component 108 is positioned less than 10 cm, less than 5, less than 3 cm, or less than 1 cm from distal tip 105. Accordingly, embodiments of component 108 having a sensor may be as disclosed in detail in U.S. Provisional Patent Application Nos. 61/745,014 and 61/745,493, both filed Dec. 21, 2012, and both entitled "Pressure-Sensing Intravascular devices, Systems and Methods", the contents of which are herein incorporated by reference in their entirety, for all purposes. Further embodiments of component 108 and intravascular device 100 may be as disclosed in U.S. Provisional Pat. Appl. No. 61/665,697, filed Jun. 28, 2012, entitled "Intravascular Devices, Systems, and Methods," the contents of which are herein incorporated by reference in their entirety, for all purposes.

In some embodiments, intravascular device 100 includes a connector 110 adjacent the proximal portion 102 of the device. In that regard, connector 110 is spaced from the proximal end 107 of flexible elongate member 130 by a distance 112. Generally, distance 112 is between 0% and 50% of the total length of flexible elongate member 130. While the total length of elongate member 130 can be any length, in some embodiments the total length is between about 1300 mm and about 4000 mm, with some specific embodiments have a length of 1400 mm, 1900 mm, and 3000 mm. Accordingly, in some instances connector 110 is positioned at the proximal end 107. In other instances, connector 110 is spaced from proximal end 107. For example, in some instances connector 110 is spaced from proximal end 107 between about 0 mm and about 1400 mm. In some specific embodiments, connector 110 is spaced from proximal end 107 by a distance of 0 mm, 300 mm, and 1400 mm.

Connector 110 is configured to facilitate communication between the intravascular device 100 and another device. More specifically, in some embodiments connector 110 is configured to facilitate communication of data obtained by component 108 to another device, such as a computing device or processor. Accordingly, in some embodiments connector 110 is an electrical connector. In such instances, connector 110 provides an electrical connection to one or more electrical conductors that extend along the length of flexible elongate member 130 and are electrically coupled to component 108. In some embodiments, connector 110 is an optical connector. In such instances, connector 110 provides an optical connection to one or more optical communication pathways (e.g., fiber optic cable) that extend along the length of flexible elongate member 130 and are optically coupled to component 108. Further, in some embodiments connector 110 provides both electrical and optical connections to both electrical conductor(s) and optical communication pathway(s) coupled to component 108. In that regard, it should again be noted that component 108 is comprised of a plurality of elements in some instances. In some embodiments, connector 110 is configured to provide a physical connection to another device, either directly or indirectly. In some embodiments, connector 110 is configured to facilitate wireless communication between intravascular device 100 and another device. Generally, any current or future developed wireless protocol(s) may be utilized. In yet other instances, connector 110 facilitates both physical and wireless connection to another device.

As noted above, in some embodiments connector 110 provides a connection between component 108 of intravascular device 100 and an external device. Accordingly, in some embodiments one or more electrical conductors, one or more optical pathways, and/or combinations thereof extend along the length of the flexible elongate member 130 between connector 110 and component 108 to facilitate communication between connector 110 and component 108. Generally, any number of electrical conductors, optical pathways, and/or combinations thereof can extend along the length of flexible elongate member 130 between connector 110 and component 108. According to some embodiments, component 108 is fixed relative to core member 135. Core member 135 slides along the LA inside elongate member 130, which remains fixed relative to the blood vessel. In some embodiments, connector 110 may be positioned as part of core element 135, at a proximal position relative to proximal end 107 of elongate member 130.

In some embodiments, component 108, a wire providing power and collecting a signal from component 108, and a conductive band subassembly in connector 110 are part of core 135. The conductive band subassembly may have approximately the same OD as elongate member 130. In such embodiments the conductive bands in connector 110 are separated from the proximal end of elongate member 130 as core 135 slides in the proximal direction, creating a gap 116. The OD of core subassembly 135 clears the inner diameter of elongate member 130, to allow for sliding.

Intravascular device 100 includes an engagement feature 150 fixed to elongate member 130 and distal relative to component 108. Accordingly, as core 135 slides in the distal direction inside elongate member 130, engagement feature 150 acts as a stop Likewise, in some embodiments locking member 150 may be the starting point as core 135 slides in the proximal direction inside elongate member 130 for pullback. In some embodiments, a second engagement feature 151 may be included proximal to engagement feature 150. Second engagement feature 151 may act as a stop for core member 135 sliding inside elongate member 130 in the proximal direction. Thus, in some embodiments, component 108 may travel along the LA inside elongated member 130 together with core member 135, from locking member 150 to locking member 151. The travel distance of component 108 may be determined according to a specific application. In general, it is desirable that the travel distance of component 108 be long enough to cover the length of a typical region of cardiovascular stenosis, or more. Some configurations may use a travel distance of about 5 cm or about 10 cm, or maybe more. Pullback distance may depend on the specific application of intravascular device 100, such as a given vasculature being inspected. For example, a coronary sliding pressure wire (for the coronary artery in the heart) may have a 20 cm sliding length to assess all positions within a deeply seated wire. On the other hand, a peripheral wire for use in blood vessels in the legs may have a sliding distance of 40 cm, 50 cm, or even more, to allow for a long enough section to be evaluated.

Embodiments consistent with the present disclosure provide the ability to retract a sensor secured to a core member to multiple locations along the length of an intravascular device without repositioning the entire intravascular device within the blood vessel. In embodiments where the sensor is a pressure sensor, blood pressure along the vessel may be mapped without losing the distal tip position. Thus, some embodiments include a pressure sensor mounted onto a sliding proximal core 135. The position of distal tip 105 may remain fixed with elongated member 130 while the sensor is pulled back with core 135. By engaging the sensor or associated mounting structure with engagement feature 150, intravascular device 100 provides the ability to torque and rotate the tip of the wire in the manner of a traditional guide wire, if desired.

Figure 2:
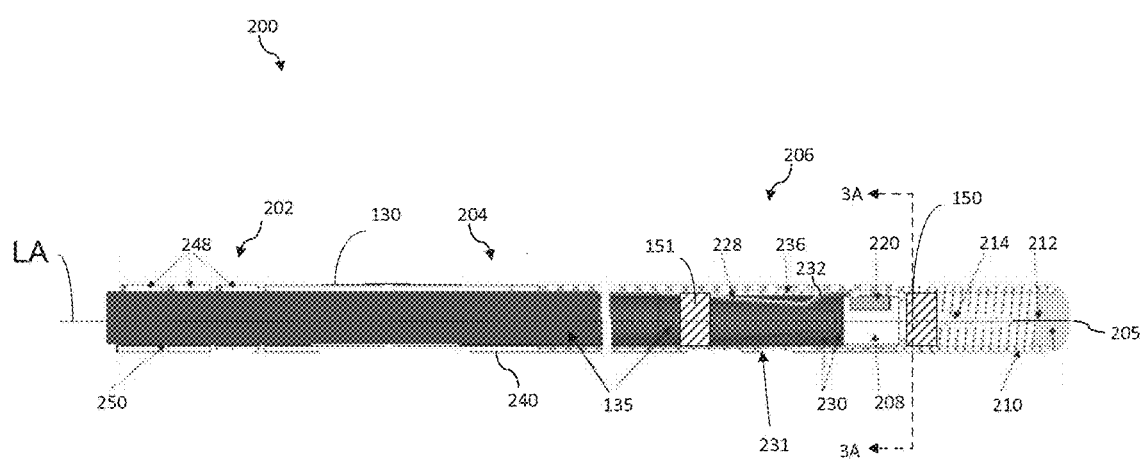
FIG. 2 is a diagrammatic cross-sectional side view of an intravascular device according to some embodiments.

FIG. 2 is a diagrammatic cross-sectional side view of an intravascular device 200 according to some embodiments. As shown, intravascular device 200 includes a proximal portion 202, a middle portion 204, and a distal portion 206. Generally, proximal portion 202 is configured to be positioned outside of a patient, while distal portion 206 and a majority of middle portion 204 are configured to be inserted into the patient, including within human vasculature. In that regard, middle and distal portion 204 and 206 have an outer diameter between about 0.0007" (0.0178 mm) and about 0.118" (3.0 mm) in some embodiments, with some particular embodiments having an outer diameter of approximately 0.014" (0.3556 mm), approximately 0.018" (0.4572 mm), or approximately 0.035" (0.889 mm). In FIG. 2, intravascular device 200 has an outer diameter of 0.014" (0.3556 mm).

In some embodiments, a pressure guide wire has a core 135 with a diameter as large as it can be while still feed a communication cable 232 through elongate element 130. In some embodiments, core 135 slides inside elongate element 130, so the core diameter may be smaller than an inner diameter (ID) of elongate member 130 to accommodate for movement within 130. In some embodiments, a clearance of 0.005" between the ID of element 130 and core 135 is enough to accommodate cable 232 leaving room to slide. In some embodiments, a wire having elongate element 130 with an OD of 0.014", core 135 would be about 0.0055" in diameter. For a wire with elongate element 130 having an OD of 0.018", core 135 would be about 0.0095" in diameter. And for a wire having elongate element 130 with an OD of 0.035", core 135 may have a diameter of about 0.0265".

As shown, distal portion 206 of intravascular device 200 has a distal tip 205. In the illustrated embodiment, distal tip 205 has a rounded profile. In some instances, distal tip 205 may include a radiopaque material such that distal tip 205 is identifiable under x-ray, fluoroscopy, and/or other imaging modalities when positioned within a patient. Accordingly, a radiopaque material is such that absorbs or reflects certain type of radiation, such as X-rays, visible radiation, or any other type of radiation used for imaging to a greater or lesser extent such that it is identified in a resulting image.

In some particular instances, distal tip 205 is solder secured to a flexible member 210 and/or a flattened tip core 212. In that regard, in some instances flexible member 210 is a coil spring. In some embodiments, flexible member 210 may be about 3 cm in length. In some embodiments, flattened tip core 212 extends distally from a distal core 214. Distal core 214 may be fixedly secured to engagement feature 150. As shown, distal core 214 tapers to a narrow profile as it extends distally towards the distal tip 207. In some instances, distal core 214 is formed of a stainless steel that has been ground down to have the desired tapered profile. In some particular instances, distal core 214 is formed of high tensile strength 304V stainless steel. In an alternative embodiment, distal core 214 is formed by wrapping a stainless steel shaping ribbon around a nitinol core. A component 208 is configured to receive and securely hold a component 220. In that regard, the component 220 is one or more of an electronic component, an optical component, and/or an electro-optical component. For example, without limitation, the component 220 may be one or more of the following types of components: a pressure sensor, a temperature sensor, an imaging element, an optical fiber, an ultrasound transducer, a reflector, a mirror, a prism, an ablation element, an RF electrode, a conductor, and/or combinations thereof. Component 220 may be referred to hereinafter as sensor circuit 220, without any limitation on the scope, as described above.

Component 220 may be mounted in several ways to core 135. In some embodiments component 220 may include a microstructure (e.g., a microfabricated layered metal component) providing alignment of the sensor and a method of attaching the structure to core 135. For example, a slot may be used for fixedly coupling core 135 to component 220 using solder, adhesive, and other materials known to those with ordinary skill in the art. Examples of methods and materials to mount component 220 to core 135 may be as disclosed in U.S. Provisional Pat. Appl. No. 61/665,697, filed Jun. 28, 2012, entitled "Intravascular Devices, Systems, and Methods," the contents of which are herein incorporated by reference in their entirety, for all purposes. Component 208 has an outer profile allowing smooth movement within the tubing in elongated member 130. A distal end of component 208 may incorporate a key feature for insertion into the engagement feature 150 that is fixedly secured to flexible member 210. The key feature in component 208 may be formed to match the key feature in the engagement feature 150.

Accordingly, engagement feature 150 may include various structural features, including combinations thereof to facilitate engagement with flexible member 210. Engagement feature 150 enables alignment and attachment of movable core 135 to flexible member 210. In some embodiments, engagement feature 150 includes a key slot that receives a key coupled to movable core 135 to allow movable core 135 to be selectively, fixedly secured to flexible member 210. For example, steering and control of flexible member 210 during positioning of the wire is dependent upon the structural integrity of movable core 135. In some instances the key feature may be incorporated into component 208 to match engagement feature 150.

In some embodiments, component 208 is disposed within flexible member 210 and/or a flexible member 130. Second engagement feature 151 may be fixedly secured to ribbon coil 231. Flexible member 130 may include ribbon coil 231 covered with a polymer coating. For example, in one embodiment the flexible member 130 is a stainless steel ribbon wire coil coated with polyethylene terephthalate (PET). In some embodiments, the flexible member 130 may be a polyimide tubing having ribbon coil 231 embedded therein. For example, in some instances a polyimide or Pebax tubing with embedded coil may be used for flexible member 130. In some particular embodiments, ribbon wire coil 250 is embedded to an inner diameter of the polyimide tubing.

Component 208 is secured to the core 135 that extends proximally from the component towards middle portion 204 and proximal portion 202 of intravascular device 200. In that regard, a distal portion 228 of core 135 may be tapered as it extends distally towards component 208. A distal end of the distal portion 228 of core 135 is fixedly secured to component 208. In some instances, the distal end of the core 226 is soldered to component 208. As shown, adhesive 230 surrounds at least a portion of distal portion 228 of core 135. In some instances, adhesive 230 is urethane acrylate, cyanoacrylate, silicone, epoxy, and/or combinations thereof; adhesive 230 is particularly suited to secure ribbon coil 231 to core 135 and component 208. In some embodiments, component 208 is fixedly secured to core 135 using solder. Different core profiles and structures along the length of an intravascular device consistent with the present disclosure may be as described in U.S. Provisional Pat. Appl. No. 61/665,697, filed Jun. 28, 2012, entitled "Intravascular Devices, Systems, and Methods," the contents of which are herein incorporated by reference in their entirety, for all purposes.

Communication cable 232 extends along the length of intravascular device 200 from proximal portion 202 to distal portion 206. In that regard, the distal end of communication cable 232 is coupled to component 220. In some embodiments, communication cable 232 is a trifilar structure as described in detail in U.S. Provisional Patent Application No. 61/665,697, filed Jun. 28, 2012, entitled "Intravascular Devices, Systems, and Methods," the contents of which are hereby incorporated by reference in their entirety, for all purposes.

Further, in some embodiments, proximal portion 202 and/or distal portion 206 incorporate spiral ribbon tubing. In some instances, the use of such spiral ribbon tubing allows a further increase in the available lumen space within the device. For example, in some instances use of a spiral ribbon tubing having a wall thickness between about 0.001" and about 0.002" facilitates the use of a core wire having an outer diameter of up to 0.0095" within a 0.014" outer diameter guide wire using a trifilar with circular cross-sectional conductor profiles. The size of the core wire can be further increased to 0.010" by using a trifilar with a flattened oblong cross-section conductor profiles. The availability of a core wire having an increased diameter allows use of materials having a lower modulus of elasticity than a standard stainless steel core wire (e.g., superelastic materials such as Nitinol or NiTiCo are utilized in some instances) without adversely affecting the handling performance or structural integrity of the guide wire and, in many instances, provides improvement to the handling performance of the guide wire, especially when a superelastic material with an increased core diameter (e.g., a core diameter of 0.0075" or greater) is utilized within the distal portion 206. According to some embodiments, a core 135 having a 0.0095" diameter may be used in a fixed pressure wire. Further according to some embodiments ribbon coil 231 may extend for the entire length of outer element 130, replacing element 240, to accommodate a core 135 having a diameter of 0.0095" or more. In such embodiments the diameter of elongated element 130 may be larger than 0.014".

Distal portion 206 of intravascular device 200 may optionally include at least one imaging marker 236. In that regard, imaging marker 236 is configured to be identifiable using an external imaging modality, such as x-ray, fluoroscopy, angiograph, CT scan, MRI, or otherwise, when distal portion 206 of intravascular device 200 is positioned within a patient. In the illustrated embodiment, imaging marker 236 may be a radiopaque coil positioned around tapered distal portion 228 of core 226. Visualization of the imaging marker 236 during a procedure provides the medical personnel an indication of the position of component 220 along a vessel. To that end, imaging marker 236 can have a known length (e.g., 0.5 cm or 1.0 cm) and/or be spaced from component 208 by a known distance (e.g., 3.0 cm) such that visualization of imaging marker 236 and/or component 208 along with the anatomical structure allows a user to estimate the position, size or length of a region of interest of the anatomical structure. Furthermore, a plurality of imaging markers 236 may be utilized in some embodiments. In that regard, in some embodiments imaging markers 236 are spaced a known distance from one another to further facilitate measuring the size or length of the region of interest.

In some embodiments core member 135 may be segmented into portions along the LA. Flexible member 240 in the illustrated embodiment is a hypotube. In some particular instances, flexible member 240 may be a stainless steel hypotube. Core member 135 is configured to slide with respect to flexible member 240.

Because sensor circuit 220 will be moving and attached to core member 135, some embodiments lock fragile electrical leads to core member 135. This may be done in intermittent locations with extremely thin-walled PET shrink tubing or in certain locations (proximal end) a thin-walled Polyimide tube. In order to be able to retract sensor circuit 220 and core member 135, a working section in flexible elongate member 130 (between the proximal hypotube and the distal tip coil) has both tensile and compression integrity and maintains the spacing and attachment between the hypotube and tip coil. This working section of flexible elongate member 130 may also maintain a reasonable cylindrical ID shape in order to move the sensor within it. In some embodiments, flexible elongate member 130 may include a thin-walled polyimide tube with integral spiral ribbon coil. The spiral coil provides additional hoop strength to the tubing to maintain the cylindrical ID shape. Having the coils embedded in polyimide provides the tensile and compression functions as the sensor is retracted and pushed forward. An alternative design to the spiral ribbon is to have three individual ribbon wires running longitudinally and embedded in the polyimide wall. In the illustrated embodiments of FIG. 2, element 231 defines the working section along which component 220 is displaced to make measurements.

In some embodiments, a proximal portion of core 135 may include conducting bands 248. In that regard, in some instances conductive bands 248 are portions of a hypotube. In other instances, conductive bands 248 are coils. Proximal portions of communication cable 232 are coupled to conductive bands 248. In that regard, in some instances each of the conductive bands is associated with a corresponding line of communication cable 232. For example, in embodiments where communication cable 232 consists of a trifilar, each of three conductive bands 248 are connected to one of the conductors of the trifilar, for example by soldering each of the conductive bands to the respective conductor. Where the communication cable 232 includes optical communication line(s), proximal portion 202 of intravascular device 200 may include an optical connector in addition to or instead of one or more of conductive bands 248. Conductive bands 248 may be part of a connector assembly positioned outside of flexible element 130, proximal to proximal end 107 of movable core 135 (cf. FIG. 1) allowing electrical connection of an external device to sensor circuit 220. In some embodiments an insulating layer or sleeve 250 separates the conductive bands 248 from core member 135. In some instances, insulating layer 250 is formed of polyimide.

Connector assembly 110 is disposed so that electrical connection is maintained during the pullback of movable core 135 relative to elongated member 130. In some embodiments conductive bands 248 are movable with respect to elongated member 130. For example, conductive bands 248 may be fixedly attached to a portion of movable core member 135.

FIG. 2 shows flexible elongate member 130 forming the exterior portion of intravascular device 200. Core member 228 slides relative to elongate member 130 along the LA, displacing component 208 along positions proximal to engagement feature 150. In some embodiments, flexible elongate member 130 may include openings in a distal portion to enable component 220 to access blood and other tissue elements in the vessel's lumen. Thus, component 220 may have acoustic, optical, or fluidic contact with blood and other tissue elements in the lumen through openings in elongate member 130 and/or flexible members 210 and 231.

In some embodiments, movable core 135 includes markings or other indicators near its proximal end. Accordingly, in some embodiments the markings provide reference positions that correlate to the relative position of component 208 and associated component 220 to flexible elongated element 130. Thus, a physician may know precisely how far the pullback of core 135 has proceeded. Some embodiments may include insulating protection of electrical leads in the proximal end of movable core 135 that would be exposed during pullback of the core.

Figure 3A:
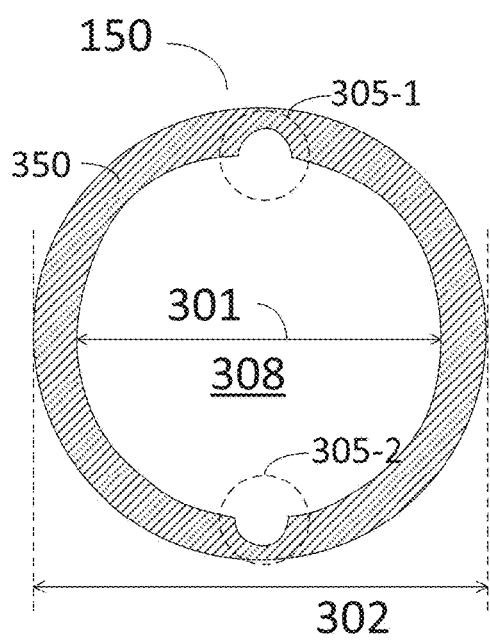
FIG. 3A is a diagrammatic cross-sectional end view of an engagement feature according to some embodiments.

FIG. 3A is a diagrammatic cross-sectional end view of engagement feature 150 taken along section line 3A-3A of FIG. 2, according to some embodiments. Engagement features as disclosed herein may include notches 305-1 and 305-2 (collectively referred hereinafter as notches 305) formed on a ring 350 having an inner diameter (ID) 301 and an outer diameter (OD) 302. In some embodiments, engagement feature 150 is a component at the proximal end of the radiopaque tip coil in flexible member 210 (cf. FIG. 2). Engagement feature 150 enables alignment and attachment anchor for the movable core to key into the component. Engagement feature 150 may also allow torqueing/rotating the tip of the wire. Engagement feature 150 includes portion 308 as an inner recess defining diameter 301, with a projection forming ring 350.

Figure 3B:
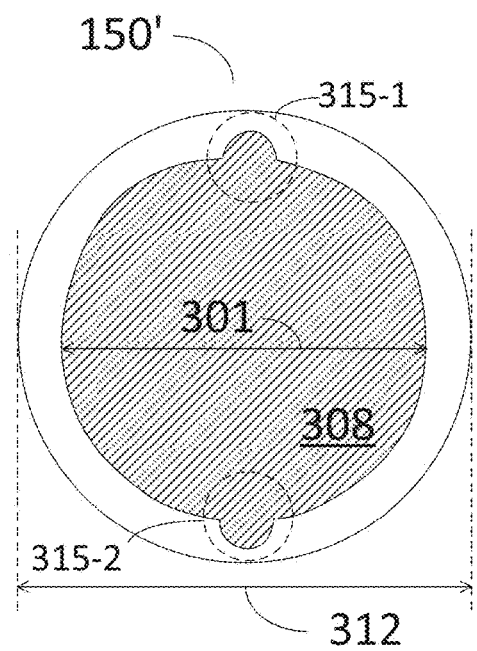
FIG. 3B is a diagrammatic cross-sectional end view of an engagement feature, according to some embodiments.

FIG. 3B is a diagrammatic cross-sectional end view of an engagement feature 150', according to some embodiments. Engagement feature 150' may be fixedly secured to element 210, just as engagement feature 150. In that regard, FIG. 3B also shows a cross-sectional view along segment 3A-3A, in FIG. 2. According to FIG. 3B, ring 305 is formed by a recess while inner portion 308 is a projection. FIGS. 3A and 3B illustrate embodiments of engagement feature 150, at the distal end of the working distance. In a similar manner, engagement feature 151 at the proximal end of the working distance may have the same cross-sectional profile as shown in FIG. 3A. Whether an engagement feature is formed as described in FIG. 3A or in FIG. 3B, component 208 has at the distal end a corresponding feature that engages feature 150 or 150'. This will be described in more detail with respect to FIG. 3C below.

Figure 3C:
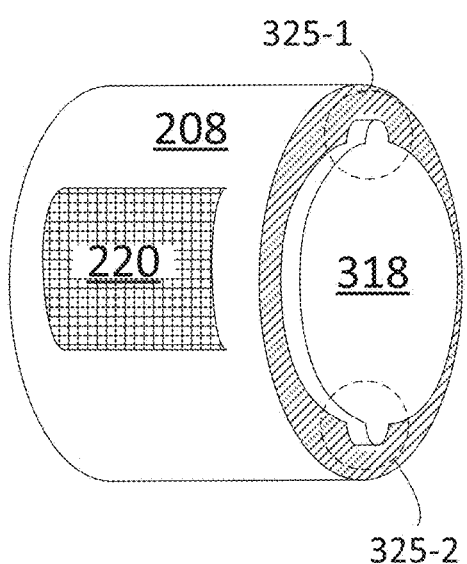
FIG. 3C is a diagrammatic perspective view of a distal portion of a component configured to interface with an engagement feature similar to that shown in FIG. 3A, according to some embodiments.

FIG. 3C is a diagrammatic perspective view of the distal end of component 208, according to some embodiments. Component 208 may include a component 220, such as a pressure sensor. Component 208 may include a distal surface 318 having an ID 311 and an OD 312. Surface 318 may include key features 325-1 and 325-2, collectively referred hereinafter as key features 325. Accordingly, distal surface 318 in component 208 may fit into engagement feature 150 by aligning feature 325-1 with feature 305-1, and feature 325-2 with feature 305-2. Thus, diameter 311 in distal surface 318 may be similar and smaller than diameter 301. Furthermore, by fitting features 325 with features 305, component 208 may provide a torque to engagement feature 150. Thus, by providing a torque to core member 135, flexible member 130 may be rotated together with core member 135. Such embodiments may be desirable when component 220 collects axially directional measurements from a blood vessel. Thus, in order to collect measurements at 360° about the LA it may be desirable to rotate component 208 together with flexible member 130. One of ordinary skill would recognize that the specific shape and configuration of features 305 and 325 is not limiting. In some embodiments features 305 and 325 may include rectangular tabs and slots that fit into each other. For example, a tab in distal surface 318 may fit into a slot in engagement feature 150, or vice versa. Furthermore, a tab and a slot in distal surface 318 may fit into a slot and a tab in engagement feature 150.

Figure 3D:
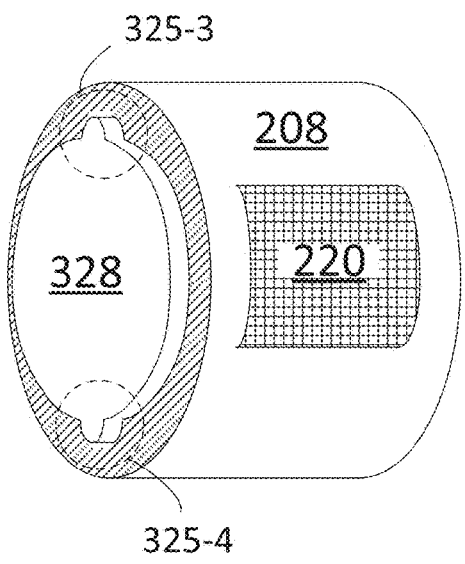
FIG. 3D is a diagrammatic perspective view of a proximal portion of the component of FIG. 3C configured to interface with an engagement feature similar to that shown in FIG. 3A, according to some embodiments.

FIG. 3D is a diagrammatic perspective view of the proximal end of component 208, according to some embodiments. Accordingly, component 208 may include proximal surface 328 having features 325-3 and 325-4. In such embodiments, proximal surface 328 may then fit into a proximal engagement feature such as proximal engagement feature 151 (cf. FIGS. 1 and 2). Thus, a pullback procedure for component 208 may stop once proximal surface 328 couples to engagement feature 151, at a proximal position. Furthermore, the locking mechanism provided by features 325-3 and 325-4 enable the rotation of elongated member 130 through a torque provided by core member 135.

Figure 4:
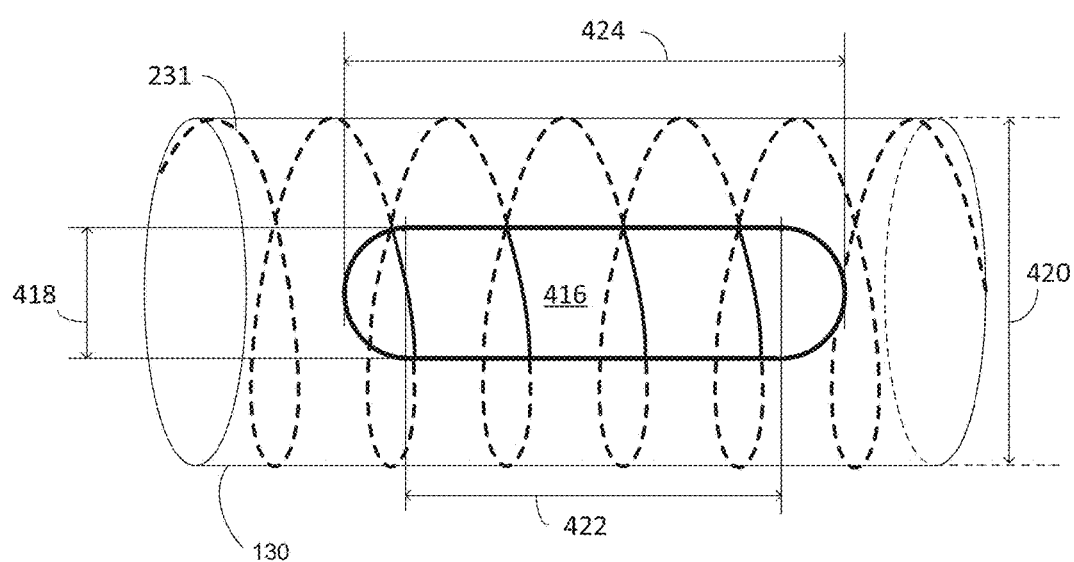
FIG. 4 shows a partial view of a flexible elongate member including an opening, according to some embodiments.

FIG. 4 shows a partial view of flexible elongate member 130 including an opening 416, according to some embodiments. In particular, a portion of flexible member 231 may be as illustrated in FIG. 4. Accordingly, an opening 416 through a sidewall of elongated member 130. Elongated member 130 may include a coil 231 that remains intact across opening 416. For example, coil 231 may be a ribbon coil keeping a circular cross sectional shape in flexible elongate member 130, enabling the sliding motion of core member 135. Alternatively, the portions of the coil extending across opening 416 may be removed, in some embodiments. Opening 416 is generally pill shaped, having elongated straight sides oriented along the LE of elongated member 130, and rounded ends. In that regard, opening 416 has a height 418 that is generally between about 25% and about 60% of a diameter 420 of elongated member 130. In one particular embodiment, elongated member 130 has an outer diameter of 0.014" and opening 416 has a height 418 of 0.0070". In some embodiments, height 418 is similar to or somewhat larger than the height of component 220 (cf. FIGS. 3C and 3D). In some embodiments, opening 416 may have any shape, including being formed by smaller openings.

A plurality of openings 416 in elongate member 130 provide portals to allow for access to vessel pressures at different locations along the LA. Openings 416 may have circular, oval, or slotted shape. A slotted shape as illustrated in FIG. 4 increases tolerance for sensor positioning while maintaining tubing integrity. Spacing of the openings 416 is dependent upon application constrains and desirability. The openings would likely be lased into the tubing, removing the polyimide material and/or the ribbon coil. Access to pressure is made via the openings and/or the spacing (depends upon pitch of the ribbon coil) of the ribbon coils. The openings may be on a single wall or potentially on opposite walls of flexible member 130. In some embodiments, openings 416 may include a series of smaller holes such that there is always some access to the fluid regardless of position of the sensor. In some embodiments component 208 may be made from a radiopaque material, such as palladium. In such configuration, a physician or operator may use component 208 for locating pressure sensing element 220.

In the illustrated embodiment, opening 416 has a length 422 and an overall length 424 including rounded end portions. The size of opening 416 ensures that component 220 has direct access to the ambient outside the intravascular device. As shown in FIG. 4, opening 416 may leave coil 231 intact. Accordingly, in some embodiments opening 416 is formed by chemically dissolving a section of the side wall of elongated member 130. In some embodiments, opening 416 is created by laser cutting the side wall of elongated member 130.

Figure 5A:
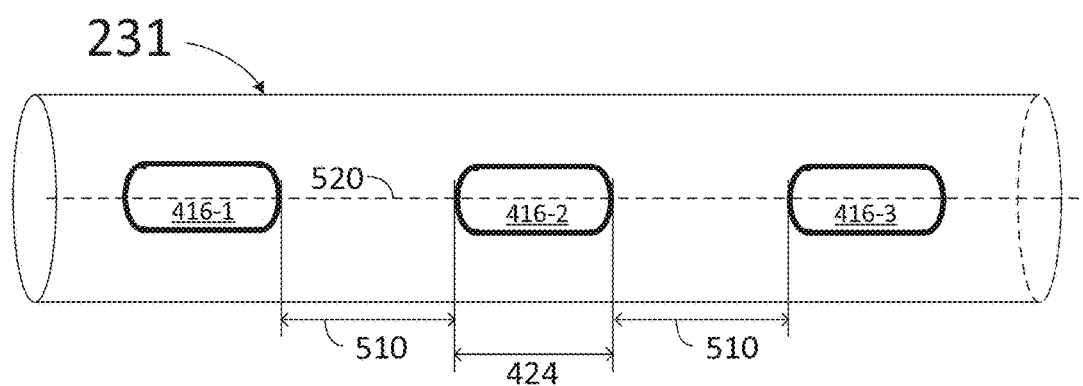
FIG. 5A shows a partial view of a flexible elongate member including a plurality of openings in a pattern, according to some embodiments.

FIG. 5A shows a partial view of flexible member 231 including a plurality of openings 416-1, 416-2, and 416-3 (hereinafter referred collectively as openings 416) in a pattern, according to some embodiments. Openings 416 may be aligned at regular intervals along axis 520. Axis 520 is substantially parallel to LA, and openings 416 are separated by a distance 510 from each other, along axis 520. Distance 510 may be 5 mm, 1 cm, 2 cm, or longer. Openings 416 may be disposed along the majority of the working section length of elongated member 130. Accordingly, it is desirable that the center of component 220 be aligned substantially along axis 520, as core 135 is displaced in a proximal direction. Thus, a pressure measurement may accurately reflect the blood pressure in an intravascular environment. To align component 220 along axis 520 during pullback, some embodiments may include structural features such as a notch or groove formed in an interior wall of flexible member 130, matching an extrusion formed in an outer diameter of component 208.

In embodiments having a sufficient number of open spaces, alignment to center of opening may not be necessary. In general, alignment conditions are relaxed as long as the fluid path to the sensor is not restricted. For example, having holes on opposite sides may open enough access radially, relaxing the conditions for the radial orientation of the sensor.

In some embodiments it is also desirable to obtain axial alignment of component 220 with openings 416. In that regard, it may be desirable to know at what position along LA core element 135 has component 220 close to the center of opening 416 along the LA. This will be described in more detail below with regard to FIG. 5B.

Figure 5B:
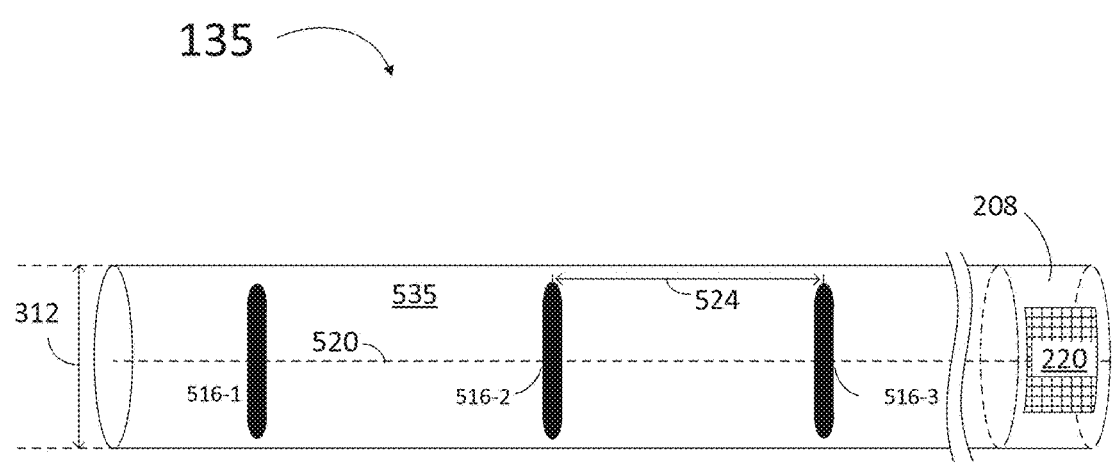
FIG. 5B shows a partial view of a core member having a pressure sensor secured thereto, according to some embodiments.

FIG. 5B shows a partial view of core member 135 including an alignment tube 535, according to some embodiments. Core member 135 may hold component 208 at a distal end, including component 220. The proximal end of alignment tube 535 may have alignment marks 516-1, 516-2, and 516-3 (collectively referred hereinafter as alignment marks 516). Alignment marks 516 form a regular pattern along axis 520 (cf. FIG. 5A). Furthermore, according to some embodiments alignment marks 516 are separated by a distance 524 approximately equal to the center-to-center distance of openings 416. Thus, in some embodiments distance 524 is approximately equal to distance 510 plus distance 424.

Accordingly, it is desirable in many applications to align the surface of component 220 close to the center of each of openings 416 during pullback of component 208. For example, in embodiments where component 220 is a pressure sensor, it is desirable that during pullback the pressure sensor faces opening 416 to accurately measure blood pressure in openings 416. Embodiments as disclosed herein may achieve alignment by ensuring that alignment marks 516 are flush with proximal end 107 of flexible member 130 (cf. FIG. 1). To enhance visibility of alignment marks 516, tube 535 may be made of a brightly colored material, while alignment marks 516 may be dark colored.

Alignment tube 535 may be a thin-walled polyimide tube around electrical wires running along the length of core 135. The polyimide tube may be formed with a first color, and alignment marks 516 may be lased holes through the tubing and/or printed on a second color contrasting the first color of the tubing. In some embodiments tube 535 is secured to core member 135 by applying adhesive through openings forming alignment marks 516.

Figure 6:
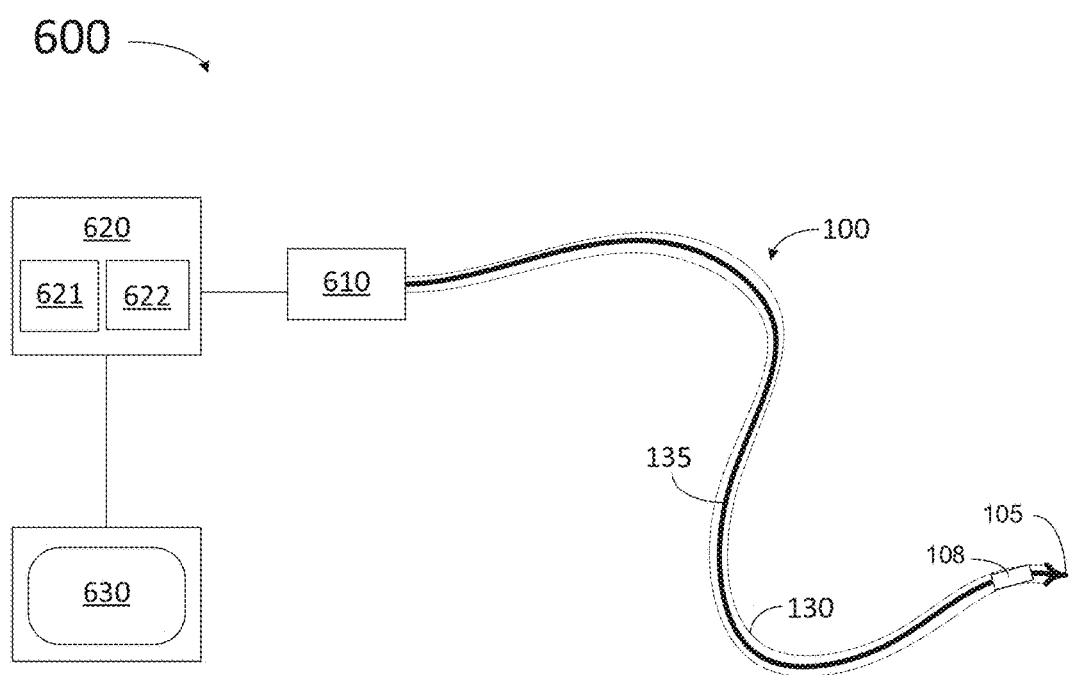
FIG. 6 shows a partial schematic view of a system for performing measurements using an intravascular device according to some embodiments.

FIG. 6 shows a partial schematic view of a system 600 for performing measurements using an intravascular device according to some embodiments. System 600 may include an intravascular device 100 having a guide wire; an interface device 610 coupled to the intravascular device; a control console 620 including a processor circuit 621 and a memory circuit 622; and a display unit 630. The guide wire in intravascular device 100 may include a core member 135, a flexible elongate member 130, and a distal tip 105, as described in detail above (cf. FIGS. 1 and 2). The distal portion of core member 135 includes component 108 holding component 220 (cf. FIGS. 1 and 2).

Interface device 610 may include electronic circuits configured to provide power and signals to component 220. Electronic circuits in interface device 610 may also be configured to receive and process signals from component 220. For example, interface device 610 may include an analog to digital converting circuit. Thus, interface device 610 may perform analog-to-digital conversion of signals provided by component 220. Console 620 may control the operation of interface device 610 by providing power and receiving the sensor circuit data processed by interface device 610. The operation of console 620 may be performed by processor circuit 621 executing commands stored in memory circuit 622. Once the data is processed and further analyzed in console 620, an image may be displayed in display unit 630. For example, an image may include a graphic display and charts representing pressure values along a longitudinal direction in a blood vessel.

Figure 7:
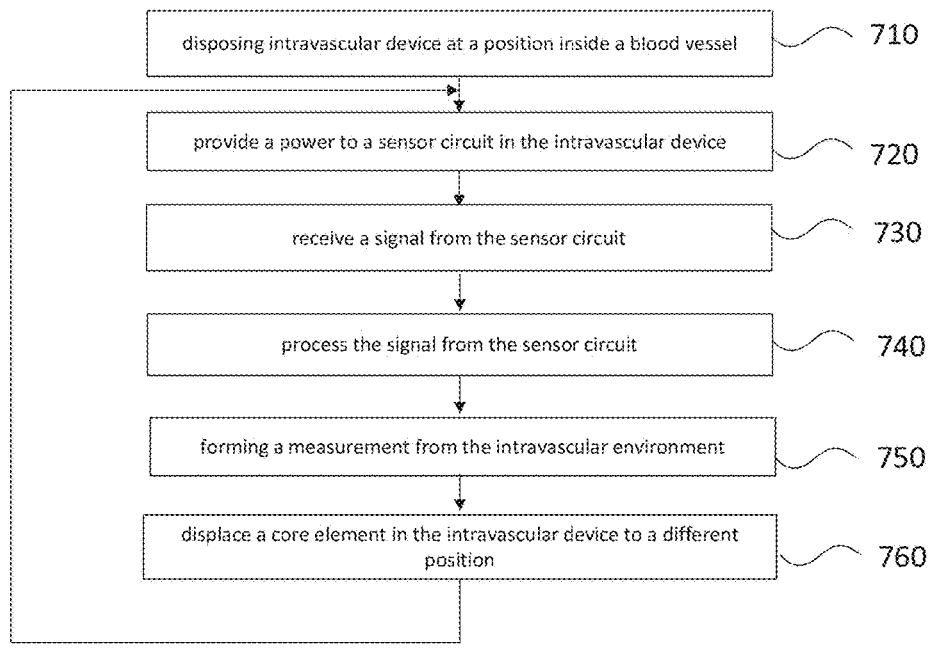
FIG. 7 shows a flow chart for a method of obtaining a measurement of an intravascular environment, according to some embodiments.

FIG. 7 shows a flow chart for a method 700 of obtaining a measurement of an intravascular environment, according to some embodiments. Method 700 may be partially performed by an operator using a system for performing measurements with a sensor exposed to an intravascular environment, as system 600 described in detail above (cf. FIG. 6). The system in method 700 may include an intravascular device having a core element, a component for a component (e.g., a sensor circuit), and a flexible member (e.g., intravascular device 100, core member 135, component 108 and component 220, FIGS. 1 and 2). Core member 135 may be configured to slide inside a flexible elongate member (e.g., elongate member 130). Thus, the flexible elongate member may be external to the core element, allowing the core member to slide inside the intravascular device. The flexible elongate member may have a plurality of openings aligned along an axis substantially parallel to a longitudinal axis of the intravascular device (e.g., openings 416 and axis 520, cf. FIGS. 4 and 5).

Furthermore, the core member in intravascular device in method 700 may include a guidewire having a cable to provide power and collect data from the sensor (e.g., cable 232). Likewise, the system in method 700 may include an interface device, a control console, and a display unit (e.g., interface device 610, console 620, and display unit 630, cf. FIG. 6). Steps in method 700 may be partially performed by the control console using a processing circuit and a memory circuit included in the console (e.g., processor circuit 621 and memory circuit 622, cf. FIG. 6).

In step 710 the intravascular device is disposed at a position inside a blood vessel. In some embodiments, step 710 may include locking the core member holding the sensor circuit to the flexible elongate element. Step 710 may also include rotating the intravascular device by providing a torque to the core element, placing the sensor circuit in a desired position within the blood vessel. In step 720 a power is provided to a sensor circuit in the intravascular device (e.g., component 220, cf. FIG. 2). In some embodiments, step 720 may include providing a voltage to a cable running along the intravascular device (e.g. cable 232, cf. FIG. 2). Further according to some embodiments, step 720 may include providing an optical power to an optical fiber in a cable running along the intravascular device. Accordingly, step 720 may be performed by the control console through the interface device.

In step 730 a signal from the sensor circuit is received. For example, the signal may be received in the interface device. In step 740 the signal from the sensor circuit is processed. For example, in some embodiments an analogue signal may be converted to a digital signal in the interface device. In step 750 a measurement from the intravascular environment is formed. Accordingly, step 750 may be partially performed using the processor circuit and the memory circuit in the control console. In some embodiments, step 750 may include storing the processed signal from the sensor circuit; and storing the position of the intravascular device inside the blood vessel. For example, the processed signal and the position of the intravascular device may be stored in the memory circuit in the control console. In some embodiments, step 750 may include displaying the measurement in the display unit.

In step 760 the core member in the intravascular device is displaced to a different position. Step 760 may include unlocking the core member from the flexible elongate member, and sliding the core member including the sensor circuit in a proximal direction relative to the distal tip of the intravascular device. Step 760 may further include keeping track of the displacement of the core member. For example, in some embodiments marks in the proximal end of the core member may indicate the displacement amount. Step 760 may include aligning the sensor circuit with the openings in the flexible elongate member, so that the sensor circuit is exposed to the blood vessel environment. For example, a certain amount of rotation of the core member may be desired, to keep alignment of the sensor circuit with an axis defining the location of the openings in the flexible elongate member (e.g., axis 520, cf. FIG. 5A).

Embodiments of the invention described above are exemplary only. One skilled in the art may recognize various alternative embodiments from those specifically disclosed. Those alternative embodiments are also intended to be within the scope of this disclosure. As such, the invention is limited only by the following claims.

What is claimed is:

1. An intravascular sensor assembly comprising:
   a flexible elongate member having a longitudinal axis (LA);
   a first engagement feature proximal to a distal end of the flexible elongate member;
   a core member disposed inside a lumen of the flexible elongate member, the core member configured to translate within the flexible elongate member along the LA proximal to the first engagement feature;
   a component holding a sensor circuit, the component fixedly secured to a distal end of the core member such that the component holding a sensor circuit translates along the LA of the flexible elongate member with the core member; and
   a second engagement feature proximal to the first engagement feature, wherein the component holding the sensor circuit is configured to translate between the second engagement feature and the first engagement feature,
   wherein the first engagement feature comprises a recess, and
   wherein the component holding the sensor circuit comprises a projection at a distal end, the projection configured to mate with the recess.

2. The intravascular sensor assembly of claim 1 wherein the flexible elongate member comprises a plurality of openings spaced along the LA, proximal to the first engagement feature.

3. The intravascular sensor assembly of claim 1 wherein the flexible elongate member comprises a hypotube and at least one flexible element fixedly coupled to a distal portion of the hypotube.

4. The intravascular sensor assembly of claim 1 wherein the core member is configured to rotate along the LA.

5. The intravascular sensor assembly of claim 1 wherein the flexible elongate member comprises a polyimide tubing.

6. An intravascular sensor assembly comprising:
   a flexible elongate member having a longitudinal axis (LA);
   an engagement feature proximal to a distal end of the flexible elongate member;
   a core member disposed inside a lumen of the flexible elongate member, the core member configured to translate within the flexible elongate member along the LA proximal to the engagement feature; and
   a component holding a sensor circuit, the component fixedly secured to a distal end of the core member such that the component holding a sensor circuit translates along the LA of the flexible elongate member with the core member;
   wherein the flexible elongate member comprises a plurality of openings spaced along the LA, proximal to the engagement feature, and wherein the core member comprises a tubing having alignment marks corresponding to the plurality of openings.

7. The intravascular sensor assembly of claim 6 wherein the alignment marks are formed at a proximal end of the core member.

* * * * *